United States Patent [19]
Franzke et al.

[11] Patent Number: 5,965,146
[45] Date of Patent: Oct. 12, 1999

[54] COSMETIC COMPOSITIONS CONTAINING WATER INSOLUBLE FIBERS

[75] Inventors: Michael Franzke, Rossdorf; Hans-Jürgen Titze, Gross-Bieberau; Karin Steinbrecht, Ober-Ramstadt; Susanne Birkel, Rossdorf, all of Germany

[73] Assignee: Wella AG, Darmstadt, Germany

[21] Appl. No.: 08/937,306

[22] Filed: Sep. 17, 1997

[30]    Foreign Application Priority Data

Sep. 28, 1996 [DE]    Germany ............................ 196 40 099

[51] Int. Cl.⁶ .............................. A61K 6/00; A61K 7/00; A61K 7/06
[52] U.S. Cl. ...................... 424/401; 424/70.1; 424/70.12
[58] Field of Search ................................ 424/401, 70.12, 424/70.11, 70.1, DIG. 2; 132/202, 207, 208

[56]    References Cited

U.S. PATENT DOCUMENTS 4,206,195   6/1980   Bolich et al. .............................. 424/16

FOREIGN PATENT DOCUMENTS 6-285449   11/1994   Japan .

OTHER PUBLICATIONS

Kuroda, *Chemical Abstracts*, vol. 125,#150746, 1995.

*Primary Examiner*—Thurman K. Page
*Assistant Examiner*—Sharon Howard
*Attorney, Agent, or Firm*—Michael J. Striker

[57]    ABSTRACT

The aqueous or aqueous/alcoholic cosmetic composition for treating, forming or maintaining a hair style includes from 0.01 to 25 percent by weight of a natural or synthetic hair fixing or thickening polymer and from 0.01 to 2.5 percent by weight of polyamide or silk fibers, each of the polyamide or silk fibers having a length of from 150 to 2000 μm or from 1 to 1100 μm respectively and a diameter of from 8 to 70 μm, so that the polyamide or silk fibers are deposited in the hair when the composition is applied to the hair. In the method of treating, forming or maintaining the hair style the composition is distributed on the hair so that the fibers are deposited in the hair and then the hair is combed, set in the hair style and dried. Other fibers including viscose, polyester, cellulose, flax linen, wool and cotton can be used instead of silk or polyamide in the composition.

12 Claims, No Drawings

COSMETIC COMPOSITIONS CONTAINING WATER INSOLUBLE FIBERS

BACKGROUND OF THE INVENTION

The present invention relates to the use of at least one water-insoluble synthetic or natural fiber material, or mixtures of fiber material, for making a cosmetic composition for treating, forming or maintaining a hair style, and also to a method of treating hair.

A pleasing appearance has always been very important. Hair style plays a particularly important role in that. Well groomed and cared for hair provides a basis for a pleasing appearance. There are a whole series of hair treatment compositions, such as shampoos, conditioners, rinses and sprayed fluids, which are applied in most different manners, for example as leave-on or rinse-off products, for cleansing and care of hair. Besides these hair care products three additional product categories are known in which the hair is changed during their use, namely permanent or temporary hair dye compositions, permanent hair shaping compositions in the form of mildly alkaline or acidic permanent shaping compositions and hair curling compositions as well as compositions, which allow only a temporary shaping and stabilization of the hair style and which are usually known as styling agents. These products include hair sprays, hair lacquers, fixing lotions, fixing foams, hair gels, luster-giving products, hair styling creams, etc. All of these compositions usually include a plurality of individual ingredients or components, which fulfill the most widely different requirements in the recipe.

It is desirable to find substances which are compatible in as many different recipes as possible. The requirements for well groomed hair include that the hair in the dry state should have a pleasing feel, elasticity, volume (except for "wetlook" hair styles) and hold. Briefly put, the hair should have a feel like hair.

SUMMARY OF THE INVENTION

It is an object of the present invention to find a new class of substances, which fulfills the above requirements. One such class of substances which is described in more detail in the following is the class of water-insoluble fibers.

It is another object of the present invention to provide cosmetic compositions for treating, forming or maintaining a hair style containing at least one water-insoluble synthetic or natural fiber, or mixtures of these fibers.

It is an additional object of the present invention to provide a method of fixing hair and forming or maintaining a hair style using a plurality of water-insoluble synthetic or natural fibers.

In the present invention to attain these objects at least one water-insoluble synthetic or natural fiber material, or their mixtures, are included in a cosmetic composition for the treatment, formation or care of a hair style or hair.

The cosmetic composition for treating, forming or maintaining a hair style according to the invention contains at least one water-insoluble synthetic or natural fiber material and at least one cosmetic ingredient.

Both synthetic and natural fibers are usable in a number of hair treatment compositions.

Man-made synthetic fibers are three-dimensional, extended, hair-like polymers or natural polymers with a clearly defined chemical structure.

Usable fibers can be synthetic fibers, such as viscose, polyester or polyamide yarn or natural fibers, such as silk cellulose, flax, linen, sheep's wool or cotton.

The synthetic fibers are characterized by their smooth fiber structure and good mechanical properties, for example, tenacity, bending resistance, etc.

Suitable polyamide fibers are, for example (poly)-hexamethylene adipamide) (Nylon 6.6, Polyamide 6.6), poly (ε-caprolactam) (Polyamide 6), polyamide 6.12 or polyamide 11.12. poly(hexamethylene adipamide) is particularly preferred. The polyamide fibers advantageously have a length of 150 to 2000 $\mu$m.

The classical polyester fibers are silk-like. Above all polyethylene terephthalates are typical suitable polymers. Also the so-called microfibers are made from polyester. Viscose fibers or also rayon fibers are made by chemical modification of cellulose. Also these viscose fibers can be used in the compositions according to the invention.

Silk fibers are preferred among the natural fibers. The silk fibers are built up from proteins (such as serine, glycine, alanine, glutamic acid, threonine, etc.). They are characterized by their smooth, shiny surfaces. When applied to the hair, they strengthen the hair and augment its luster. The water retention value, which is about 42 percent, is outstanding, so that the moisture uptake amounts to about 11 percent, which is approximately that of the hair. The silk fibers advantageously each have a length of from 1 to 1100 $\mu$m.

Mixtures of the above-mentioned synthetic fibers with natural fibers in different proportions can also be used in the compositions according to the invention.

The fibers are characterized by a hair-like structure, especially the natural fibers. They are deposited in the hair and strengthen the hold of the hair style. This was established by measurement of the breaking force. The fibers have advantageously a diameter of 8 $\mu$m to 70 $\mu$m, especially preferred is from 10 $\mu$m to 30 $\mu$m. Their lengths advantageously are between 20 $\mu$m to 2000 $\mu$m, especially from 150 $\mu$m to 750 $\mu$m is particularly preferred.

The cosmetic composition according to the invention preferably contains a plurality of the fibers in an amount of from 0.01 to 2.5 percent by weight, especially from 0.05 to 1 percent by weight. The composition according to the invention can advantageously be in the form of a hair fixing, hair dyeing, tinting or bleaching composition. The composition can be applied as a lotion, cream, milk, gel, cream, gel foam and spray.

The composition according to the invention can furthermore contain any of the conventional cosmetic ingredients commonly used in hair treatment compositions, for example, solvents, such as water and lower aliphatic alcohols, e.g. ethanol, propanol and isopropanol, or glycols, such as glycerol and 1,2-propylene glycol; wetting agents or emulsifiers from the classes of anionic, cationic, amphoteric or non-ionic surfactants, such as fatty alcohol sulfates, alkyl benzene sulfonates, alkyltrimethylammonium salts, moisturizing agents, alkylbetaines, ethoxylated fatty alcohols, ethoxylated nonylphenols, fatty acid alkanol amides, ethoxylated fatty acid esters, in an amount of from 0.1 to 30 percent by weight; perfume oils, in an amount of from 0.1 to 0.5 percent by weight; turbidity-inducing agents, such as ethylene glycol distearate, in an amount of from about 0.2 to 5.0 percent by weight; pearlescence inducing agents, such as a mixture of fatty acid monoalkylolamides and ethylene glycol distearate, in an amount of about 1.0 to 10 percent by weight; bactericidal and fungicidal ingredients, such as 2,4,4-trichloro-2-hydroxydiphenyl ether or methylchloroisothiazoline, in an amount of from 0.01 to 1.0 percent by weight; thickeners, such as coconut oil fatty acid diethanolamide, in an amount of from about 0.2 to 3.0 percent by weight; buffer substances, such as sodium citrate or sodium phosphate, in an amount of 0.1 to 1.0 percent by weight; solvating agents, such as ethoxylated castor oil, in an amount of about 0.1 to 1.0 percent by weight; dye compounds, such as fluorescein-sodium salt, in an amount of about 0.1 to 1.0 percent by weight; hair care materials, such as plant and herb extracts, protein and silk hydrolyzates, cationic resin, lanolin derivatives, in an amount of 0.1 to 5 percent by weight; physiologically compatible silicon derivatives, such as silicone oil, silicone polymers and siloxanes; light protective agents; anti-oxidants; radical trapping agents; anti-flaking agents, in an amount of about 0.01 to 2 percent by weight; physiologically compatible organic acids, such as formic acid, glyoxylic acid, lactic acid, tartaric acid and citric acid; natural, modified-natural or synthetic polymers, such as shellac, cationic, anionic, nonionic and amphoteric polymers, hydroxyalkyl cellulose, chitosan, chitin or chitosan derivatives; direct-dyeing hair dye compounds; oxidation hair dye compounds which are developed oxidatively; oxidizing agents; fatty alcohols; luster-enhancing substances; vitamins; softeners; combability improving agents; defatting agents; anti-foaming agents and propellant gases, for example fluorocarbons, dimethyl ether, hydrocarbons and compressible gases.

The hair-do or hair style lasts longer and is improved because of the improved fixing properties due to the addition of the fiber.

In a preferred embodiment the composition according to the invention contains additionally at least one natural and/or synthetic polymer, which is selected from the group of fixing and thickening polymers. The polymers can be used in an amount of 0.01 to 25 percent by weight, preferably from 0.01 to 20 percent by weight and can be present in dissolved form or as a dispersion. Hair fixing compositions can be used containing fixing polymers and added fibers.

The cosmetic composition according to the invention can be sprayed using a propellant or with the help of a mechanically operated spraying device or can be dispensed as a foam with the help of a foam producing device. For that special valves can be used.

If the cosmetic composition is sprayed with the help of a propellant, it preferably contains from 3 to 75 percent by weight of a propellant and is filled in a pressurized container.

Suitable propellants include, for example, lower alkanes, such as n-butane, i-butane and propane or their mixtures or also dimethyl ether and fluorocarbons, such as F 152 (1,1-difluoroethane) or F 134 (tetrafluoroethane) and further gaseous propellants under pressure, such as $N_2$, $N_2O$ and $CO_2$ and mixtures of these propellants.

Mechanical spraying apparatuses or foam producing apparatus are those which facilitate production of a spray or foam of a liquid without using a propellant. For example a spray pump for powder, or an elastic container provided with a spray valve in which the cosmetic composition according to the invention is filled under pressure, can be used as suitable mechanical spraying devices. The elastic container is thus stretched during filling so that the composition will be continuously dispensed when the spray valve is opened because of contraction of the elastic container.

When the cosmetic composition according to the invention is used for hair fixing, the following steps are taken: After the hair is washed, from 5 to 30 g of composition is distributed on the hair according to the amount of hair present. Subsequently the hair is combed and set to from the hair-do or hair style and dried.

The composition according to the invention can be, for example a liquid fixing agent, a foam fixing agent, a hair gel or also a hair spray. More hold results because of the strengthening action of the fibers in the hair after using the hair fixing composition according to the invention.

A hair dyeing composition according to the invention contains 0.05 to 3 percent by weight colored or colorless fibers and 0.05 to 2.0 percent by weight of at least one direct-dyeing hair dye compound, which, for example, can be selected from the following classes of direct-dyeing dye compounds: aromatic nitro dye compounds, e.g. 1,4-diamino-2-nitrobenzene; azo dye compounds, such as Acid Brown 4 (C.I. 14 805); anthraquinone dye compounds, Disperse Violet 4 (C.I. 61 105); and triphenylmethane dye compounds, for example Basic Violet 1 (C.I. 42 535). These dye compounds can have an acidic, basic or non-ionic character according to their substituents. These direct-dyeing dye compounds can also include natural dye compounds, such as Henna or Reng, which do not require oxidation to develop.

Hair treated with the compositions according to the invention is satisfactorily fixed and has great springiness with a simultaneously natural feel and silky luster in the dry state.

The following examples should serve to illustrate tine compositions according to the invention, without limiting the claims appended hereinbelow.

EXAMPLES

The following fibers were used in the following exemplary compositions:

Silk fiber (1): silk fiber with a fiber length between 1 and 160 μm (Crosilk Powder marketed by Croda, Germany)

Silk fiber (2): silk fiber with a fiber length between 200 and 720 μm (marketed by Interorgana, Germany)

Silk fiber (3): silk fiber with a fiber length between 260 and 1100 μm (marketed by Interorgana, Germany)

Polyamide fiber: poly(hexamethleneadipamide) (Nylon 6.6) with a fiber length between 150 and 2000 μm (marketed by STW Schwarzwälder Textile Works, Germany)

Viscose fiber: viscose fiber with a fiber length between 150 and 2000 μm (marketed by REO Flock & Fiber, Germany)

Example 1

Hair Balsam

| | |
|---|---|
| 0.50 g | silk fiber (1) |
| 6.00 g | glyceryl stearate/polyethylene glycol-(20)-cetearyl ether |
| 4.00 g | diquaternary polydimethylsiloxane (Abil ® Quat 3272 of Goldschimdt, Germany) |
| 2.00 g | cetyl alcohol |
| 1.36 g | citric acid |
| 0.14 g | 1,2-dibromo-2,4-dicyanobutane |
| 0.12 g | perfume |
| 85.88 g | water |
| 100.0 g | |

Example 2

Hair Rinse

| | |
|---|---|
| 0.75 g | polyamide fiber |
| 4.00 g | cetylstearyl alcohol |
| 1.36 g | DL-2-pyrrolidone-5-carboxylic acid |
| 0.75 g | cetyltrimethylammonium chloride |
| 0.50 g | perfume |

-continued

```
0.20 g  plant extract (Extrapon ® 5 Special of
        Dragoco/Germany)
92.44 g water 100.00 g
```

Example 3

Sprayable Hair Care Composition

```
0.15 g  silk fiber (1)
2.00 g  dimethyldiallylammonium chloride
1.25 g  polyethylenglycol-(40)-sorbitan-
        monopalmitate
1.00 g  DL-2-pyrrolidone-5-carboxylic acid
0.10 g  perfume
0.03 g  cetyltrimethylammonium chloride
15.15 g ethanol
80.32 g water 100.00 g
```

Example 4

Foam-forming Hair Care Composition

```
0.40 g  silk fiber (2)
2.00 g  cationic emulsion of amine functionalized
        polydimethylsiloxane(929 Cationic Emulsion of
        Dow Corning Europe/Belgium)
1.30 g  citric acid
0.50 g  hydroxypropylcellulose (M = 1,150,000 g/mol)
0.30 g  silicone wax (2501 Cosmetic Wax of Dow
        Corning, Belgium)
0.20 g  perfume
0.25 g  cetyltrimethylammonium chloride
0.15 g  D-panthenol
0.10 g  elastin hydrolyzate
5.00 g  propane/butane (5.0 bar)
10.00 g ethanol
79.80 g water 100.00 g
```

Example 5

Hair Fixing Composition

```
0.10 g  silk fiber (3)
2.00 g  vinylpyrrolidone/vinylacetate copolymer
0.90 g  formic acid
0.20 g  1,2-propylene glycol
0.15 g  perfume
0.03 g  cetyltrimethylammonium chloride
20.20 g water
75.42 g ethanol 100.00 g
```

Example 6

Hair Fixing Composition

```
0.25 g  polyamide fiber
0.25 g  silk fiber (2)
3.00 g  vinylpyrrolidone/vinylacetate copolymer
0.90 g  formic acid
0.20 g  1,2-propylene glycol
0.15 g  perfume
0.03 g  cetyltrimethylammonium chloride
20.00 g water
75.22 g ethanol 100.00 g
```

Example 7

Hair Fixing Composition

```
0.20 g  silk fiber (1)
3.00 g  vinylpyrrolidone/vinylacetate copolymer
0.90 g  formic acid
0.20 g  1,2-propylene glycol
0.15 g  perfume
0.03 g  cetyltrimethylammonium chloride
20.30 g water
75.22 g ethanol 100.00 g
```

Example 8

Hair Fixing Composition

```
0.10 g  viscose fiber
3.00 g  vinylpyrrolidone/vinylacetate copolymer
0.90 g  formic acid
0.20 g  1,2-propylene glycol
0.15 g  perfume
0.03 g  cetyltrimethylammonium chloride
20.20 g water
75.42 g ethanol 100.00 g
```

Example 9

Sunscreen with UV-Protection

```
0.15 g  silk fiber (2)
2.15 g  DL-2-pyrrolidone-5-carboxylic acid
1.50 g  vinylpyrrolidone/vinylacetate copolymer
1.25 g  vinylpyrrolidone/dimethylaminoethyl-
        methacrylate copolymer
0.20 g  perfume
0.15 g  glycerol (85 percent)
0.10 g  2-hydroxy-4-methoxybenzophenone
42.90 g water
51.60 g ethanol 100.0 g
```

Example 10

Hair Care Fixing Lotion

| | |
|---|---|
| 0.25 g | silk fiber (3) |
| 4.00 g | vinylpyrrolidone/vinylacetate copolymer |
| 1.20 g | DL-2-pyrrolidone-5-carboxylic acid |
| 0.40 g | hydrogenated castor oil, ethoxylated with 40 Mol ethylene oxide |
| 0.20 g | perfume |
| 93.95 g | water |
| 100.00 g | |

Example 11

Foam Fixing Composition with Strong Fixing

| | |
|---|---|
| 0.2 g | polyamide fiber |
| 5.00 g | vinylpyrrolidone/vinylacetate copolymer |
| 0.60 g | DL-2-pyrrolidone-5-carboxylic acid |
| 0.45 g | glyceryl laurate |
| 0.15 g | perfume |
| 0.06 g | cetyltrimethylammonium chloride |
| 5.00 g | propane/butane (5.0 bar) |
| 10.40 g | ethanol |
| 77.74 g | water |
| 100.00 g | |

Example 12

Foam Fixing Composition

| | |
|---|---|
| 0.10 g | silk fiber (3) |
| 1.80 g | chitosan |
| 1.10 g | formic acid |
| 0.20 g | 1,2-propylene glycol |
| 0.20 g | perfume |
| 0.10 g | cetyltrimethylammonium chloride |
| 6.00 g | propane/butane (5.0 bar) |
| 10.20 g | ethanol |
| 80.30 g | water |
| 100.00 g | |

Example 13

Foam Fixing Composition

| | |
|---|---|
| 0.25 g | viscose fiber |
| 3.15 g | polyvinylpyrrolidone |
| 1.60 g | citric acid |
| 0.60 g | hydrogenated castor oil, ethoxylated with 40 Mol ethylene oxide |
| 0.22 g | decylpolyglucoside |
| 0.20 g | vinylpyrrolidone/methacrylamidopropyl-trimethylammonium chloride |
| 0.20 g | perfume |
| 6.00 g | propane/butane (5.0 bar) |
| 87.78 g | water |
| 100.00 g | |

Example 14

Foam Fixing Composition

| | |
|---|---|
| 0.05 g | silk fiber (2) |
| 2.20 g | vinylimidazolium methochloride/1-vinyl-2-pyrrolidone copolymer |
| 1.00 g | glucose syrup |
| 0.70 g | oleylpolyethylene glycol-(200)-ether |
| 0.60 g | citric acid |
| 0.10 g | perfume |
| 7.00 g | propane/butane (5.0 bar) |
| 10.20 g | ethanol |
| 78.15 g | water |
| 100.00 g | |

Example 15

Care-Giving Foam Fixing Composition

| | |
|---|---|
| 0.2 g | silk fiber (3) |
| 6.0 g | vinylcaprolactam/vinylpyrrolidone/dimethylaminoethylmethacrylate terpolymer |
| 0.6 g | formic acid |
| 0.2 g | cetyltrimethylammonium chloride |
| 0.2 g | hydrogenated castor oil, ethoxylated with 45 Mol ethylene oxide |
| 0.2 g | perfume |
| 96.0 g | water |
| 100.0 g | |

The mixture is dispensed with a propane/butane propellant gas mixture in a ratio of 94:6.

Example 16

Dyeing and Fixing Composition

| | |
|---|---|
| 0.23 g | silk fiber (1) |
| 2.50 g | vinylacetate/crotonic acid/polyglycol copolymer |
| 0.20 g | perfume |
| 0.07 g | 1-amino-4-(2',3'-dehydroxypropyl)amino-5-chloro-2-nitrobenzene |
| 0.05 g | Basic Brown 17 (C.I. 12 251) |
| 0.01 g | Basic Blue 7 (C.I. 42 595) |
| 0.0023 g | Basic Violet 14 (C.I. 42 510) |
| 46.94 g | water |
| 50.00 g | ethanol |
| 100.0 g | |

Example 17

Hair Spray with Strong Fixing Effect

| | |
|---|---|
| 0.15 g | silk fiber (3) |
| 5.00 g | t-octylacrylamide/acrylic acid/t-butyl-aminoethylmethacrylate terpolymer |
| 0.58 g | 2-amino-2-methyl-1-propanol |
| 0.15 g | perfume |
| 40.00 g | propane/butane 1.5 |
| 54.12 g | ethanol |
| 100.00 g | |

Example 18

Hair Spray

| | |
|---|---|
| 0.05 g | polyamide fiber |
| 3.50 g | vinylacetate/crotonic acid/vinylneodecanoate terpolymer |
| 0.15 g | perfume |
| 0.14 g | formic acid |
| 45.00 g | dimethyl ether |
| 51.16 g | ethanol |
| 100.00 | |

Example 19

Styling-Hair Spray

| | |
|---|---|
| 0.10 g | silk fiber (2) |
| 6.50 g | vinylpyrrolidone/vinylacetate copolymer |
| 0.17 g | formic acid |
| 0.10 g | perfume |
| 10.67 g | butane (1.5 bar) |
| 33.33 g | propane/butane |
| 43.13 g | ethanol |
| 100.00 | |

Example 20

80% VOC-Hair Spray

| | |
|---|---|
| 0.10 g | polyamide fiber |
| 0.10 g | silk fiber (3) |
| 4.00 g | t-butylacrylate/ethylacrylate/methacrylic acid terpolymer |
| 0.72 g | 2-amino-2-methyl-1-propanol |
| 0.20 g | cyclotetra(dimethylsiloxane) |
| 0.05 g | perfume |
| 15.00 g | water |
| 39.83 g | ethanol |
| 40.00 g | dimethyl ether |
| 100.00 g | |

Example 21

Pump Spray

| | |
|---|---|
| 0.05 g | polyamide fiber |
| 4.50 g | t-octylacrylamide/acrylic acid/t-butyl-aminoethylmethacrylate terpolymer |
| 0.52 g | 2-amino-2-methyl-1-propanol |
| 0.30 g | perfume |
| 0.10 g | dimethylsiloxane/ethyleneglycol copolymer |
| 6.53 g | water |
| 88.00 g | ethanol |
| 100.00 g | |

Example 22

80% VOC-Pump Spray

| | |
|---|---|
| 0.075 g | silk fiber (1) |
| 5.00 g | vinylpyrrolidone/vinylacetate copolymer |
| 0.30 g | perfume |
| 0.26 g | formic acid |
| 13.84 g | water |
| 80.525 g | ethanol |
| 100.000 g | |

Example 23

55% VOC-Pump Spray

| | |
|---|---|
| 0.10 g | viscose fiber |
| 3.50 g | vinylacetate/crotonic acid copolymer |
| 0.28 g | formic acid |
| 0.20 g | perfume |
| 40.23 g | water |
| 55.69 g | ethanol |
| 100.00 g | |

Example 24

Hair Gel

| | |
|---|---|
| 0.20 g | silk fiber (1) |
| 2.50 g | hydroxypropylmethylcellulose |
| 0.80 g | polyoxyethylene-(20)-sorbitan monopalmitate |
| 0.50 g | polyoxyethylene-(25)-p-aminobenzoic acid |
| 0.40 g | formic acid |
| 0.12 g | cis-1-(3-chloroallyl)-3,5,7-triaza-1-azoniaadamantane chloride |
| 0.10 g | perfume |
| 23.00 g | glycerol (86 percent) |
| 72.38 g | water |
| 100.00 g | |

Example 25

Fixing Hair Styling Gel

| | |
|---|---|
| 0.1 g | polyamide fiber |
| 2.50 g | polyvinyl pyrrolidone |
| 2.00 g | hydroxypropyl-guar |
| 0.80 g | hydrogenated castor oil, ethoxylated with 45 Mol ethylene oxide |
| 0.60 g | DL-2-pyrrolidone-5-carboxylic acid |
| 0.45 g | sodium benzoate |
| 0.30 g | hydroxyethylcellulose |
| 0.20 g | perfume |
| 0.09 g | sodium formate |
| 0.05 g | mica/titan oxide/tin oxide powder (Soloron ®) Silver Sparkle of Merck, Germany) |
| 92.91 g | water |
| 100.00 g | |

Example 26

Hair Fixing Liquid-Gel

| | |
|---|---|
| 0.15 g | silk fiber (2) |
| 3.00 g | vinylpyrrolidone/vinylacetate copolymer |
| 1.80 g | polyoxyethylene-(20)-sorbitan monopalmitate |
| 1.35 g | polyethylene glycol-(45) |
| 1.05 g | hydroxyethyl cellulose |
| 1.00 g | citric acid |
| 0.20 g | 1,2-dibromo-2,4-dicyanobutane |
| 0.20 g | perfume |
| 91.25 g | water |
| 100.00 g | |

Unless otherwise indicated all above-stated percents are by weight.

The disclosure in German Patent Application 196 40 099.6 of Sep. 28, 1996 is incorporated here by reference. This German Patent Application describes the invention described hereinabove and claimed in the claims appended hereininbelow and provides the basis for a claim of priority for the instant invention under 35 U.S.C. 119.

While the invention has been illustrated and described as embodied in cosmetic compositions containing water-insoluable fibers for treating, shaping or caring for hair, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

1. A cosmetic composition for treating, forming or maintaining a hair style, said composition comprising
   at least one cosmetic ingredient,
   and a plurality of fibers, each of said fibers having a length of from 20 to 2000 $\mu$m and a diameter of from 8 to 70 $\mu$m and consisting of at least one water-insoluble synthetic or natural fiber material, so that said fibers are deposited in hair when said composition is applied to the hair.

2. The cosmetic composition as defined in claim 1, wherein said at least one water-insoluble fiber material is selected from the group consisting of viscose, polyester, polyamide, silk, cellulose, flax, linen, sheep's wool and cotton.

3. The cosmetic composition as defined in claim 1, wherein said length of each of said fibers is from 150 to 750 $\mu$m and said diameter is from 10 $\mu$m to 30 $\mu$m.

4. The cosmetic composition as defined in claim 1, wherein said at least one water-insoluble fiber material is present in an amount of from 0.01 to 2.5 percent by weight.

5. The cosmetic composition as defined in claim 4, wherein said amount of said at least one water-insoluble fiber material is from 0.05 to 1 percent by weight.

6. The cosmetic composition as defined in claim 1, wherein said at least one cosmetic ingredient comprises at least one member selected from the group consisting of natural thickening polymers, synthetic thickening polymers, natural hair fixing polymers and synthetic hair fixing polymers.

7. The cosmetic composition as defined in claim 6, wherein said at least one cosmetic ingredient includes perfume and a solvent selected from the group consisting of water, ethanol, propanol and isopropanol, and wherein said at least one water-insoluble fiber material is present in an amount of from 0.01 to 2.5 percent by weight.

8. The cosmetic composition as defined in claim 7, further comprising at least one propellant selected from the group consisting of $N_2O$, $N_2$, $CO_2$, n-butane, i-butane, propane, dimethyl ether and fluorocarbons.

9. The cosmetic composition as defined in claim 1, in the form of a hair fixing preparation, a hair dyeing preparation and a hair care preparation.

10. A cosmetic composition for treating, forming or maintaining a hair style, said composition comprising
    from 0.01 to 25 percent by weight of a hair fixing polymer;
    at least one cosmetic ingredient comprising at least one solvent selected from the group consisting of water and ethanol;
    and from 0.01 to 2.5 percent by weight of a plurality of polyamide fibers, each of said polyamide fibers having a length of from 150 to 2000 $\mu$m and a diameter of from 8 to 70 $\mu$m, so that said polyamide fibers are deposited in hair when said composition is applied to the hair.

11. A cosmetic composition for treating, forming or maintaining a hair style, said composition comprising
    from 0.01 to 25 percent by weight of a hair fixing polymer;
    at least one cosmetic ingredient comprising at least one solvent selected from the group consisting of water and ethanol;
    and from 0.01 to 2.5 percent by weight of a plurality of silk fibers, each of said silk fibers having a length of from 1 to 1100 $\mu$m and a diameter of from 8 to 70 $\mu$m, so that said silk fibers are deposited in hair when said composition is applied to the hair.

12. A method of fixing hair and forming or maintaining a hair style, said method comprising the steps of:
    a) distributing from 5 to 30 g of a hair fixing composition comprising water, at least one synthetic or natural hair fixing polymer and a plurality of fibers on the hair according to the amount of the hair present so that said fibers are deposited in the hair; and
    b) subsequently combing the hair, setting the hair in the hair style and drying the hair;
    wherein each of said fibers has a length of from 20 to 2000 $\mu$m and a diameter of from 8 to 70 $\mu$m and consists of at least one water-insoluble synthetic or natural fiber material selected from the group consisting of viscose, polyester, polyamide, silk, cellulose, flax linen, sheep's wool and cotton.

* * * * *